(12) United States Patent
Wang et al.

(10) Patent No.: US 12,230,019 B2
(45) Date of Patent: Feb. 18, 2025

(54) DECOUPLING DIVIDE-AND-CONQUER FACIAL NERVE SEGMENTATION METHOD AND DEVICE

(71) Applicant: ZHEJIANG UNIVERSITY, Hangzhou (CN)

(72) Inventors: Jing Wang, Hangzhou (CN); Bo Dong, Hangzhou (CN); Hongjian He, Hangzhou (CN); Xiujun Cai, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 17/802,953

(22) PCT Filed: Feb. 28, 2022

(86) PCT No.: PCT/CN2022/076927
§ 371 (c)(1),
(2) Date: Aug. 28, 2022

(87) PCT Pub. No.: WO2023/045231
PCT Pub. Date: Mar. 30, 2023

(65) Prior Publication Data
US 2024/0203108 A1    Jun. 20, 2024

(30) Foreign Application Priority Data
Sep. 22, 2021    (CN) .............................. 202111106992

(51) Int. Cl.
*G06V 10/80*    (2022.01)
*A61B 34/10*    (2016.01)
(Continued)

(52) U.S. Cl.
CPC ............ *G06V 10/806* (2022.01); *A61B 34/10* (2016.02); *G06V 10/26* (2022.01); *G06V 10/761* (2022.01);
(Continued)

(58) Field of Classification Search
None
See application file for complete search history.

(56) References Cited

U.S. PATENT DOCUMENTS 11,816,881 B2 * 11/2023  Paik ................... G06V 10/7715
2010/0183222 A1   7/2010  Fattal
(Continued)

FOREIGN PATENT DOCUMENTS

| CN | 112102321 | 12/2020 |
| CN | 112465827 | 3/2021 |
| CN | 112862805 | 5/2021 |

OTHER PUBLICATIONS

Wang, Xiaohong, and Xudong Jiang. "Retinal vessel segmentation by a divide-and-conquer funnel-structured classification framework." Signal processing 165 (2019): 104-114. (Year: 2019).*
(Continued)

*Primary Examiner* — Michelle M Entezari Hausmann
(74) *Attorney, Agent, or Firm* — Jiwen Chen; Joywin IP Law PLLC

(57) ABSTRACT

The present invention discloses a decoupling divide-and-conquer facial nerve segmentation method and device. As for the characteristics of a small facial nerve structure and a low contrast, a facial nerve segmentation model including a feature extraction module, a rough segmentation module, and a fine segmentation module is constructed. The feature extraction module is configured to extract a low-level feature and a plurality of different- and high-level features. The rough segmentation module is configured to globally search
(Continued)

the different- and high-level features for facial-nerve features and fuse them. The fine segmentation module is configured to decouple a fused feature to obtain a central body feature. After the central body feature is combined with the low-level feature to obtain an edge-detail feature, a space attention mechanism is used to extract attention features from the central body feature and the edge-detail feature, to obtain a facial nerve segmentation image. The method improves the precision and speed of automatic facial nerve segmentation, and meets the needs of preoperative path planning for robotic cochlear implantation.

10 Claims, 6 Drawing Sheets

(51) Int. Cl.
*G06V 10/26* (2022.01)
*G06V 10/74* (2022.01)
*G06V 10/77* (2022.01)
*G06V 10/776* (2022.01)
*G06V 20/70* (2022.01)

(52) U.S. Cl.
CPC ........ *G06V 10/7715* (2022.01); *G06V 10/776* (2022.01); *G06V 20/70* (2022.01); *A61B 2034/107* (2016.02); *G06V 2201/03* (2022.01)

(56) References Cited

U.S. PATENT DOCUMENTS

| | | | |
|---|---|---|---|
| 2011/0248988 A1* | 10/2011 | Park | H04N 13/261 |
| | | | 382/190 |
| 2017/0011281 A1* | 1/2017 | Dijkman | G06V 10/768 |
| 2020/0356842 A1* | 11/2020 | Guo | G06V 20/20 |
| 2022/0076035 A1* | 3/2022 | Wu | G06V 30/194 |
| 2022/0092387 A1* | 3/2022 | Le | G06N 3/006 |
| 2023/0057261 A1* | 2/2023 | Liu | H04N 19/184 |

OTHER PUBLICATIONS

Zhao, Junyong, et al. "MSEF-Net: Multi-scale edge fusion network for lumbosacral plexus segmentation with MR image." Artificial Intelligence in Medicine 148 (2024): 102771. (Year: 2024).*
Dong, Bo, et al. "Towards accurate facial nerve segmentation with decoupling optimization." Physics in Medicine & Biology 67.6 (2022): 065007. (Year: 2022).*
Du, Chaoben, and Shesheng Gao. "Image segmentation-based multi-focus image fusion through multi-scale convolutional neural network." IEEE access 5 (2017): 15750-15761. (Year: 2017).*
Cao, Yuan, et al. "MBANet: A 3D convolutional neural network with multi-branch attention for brain tumor segmentation from MRI images." Biomedical Signal Processing and Control 80 (2023): 104296. (Year: 2023).*
Xu, Geng-Xin, and Chuan-Xian Ren. "SPNet: A novel deep neural network for retinal vessel segmentation based on shared decoder and pyramid-like loss." Neurocomputing 523 (2023): 199-212. (Year: 2023).*

* cited by examiner

Facial nerve 3D label          Facial nerve 3D prediction
                                       result

DECOUPLING DIVIDE-AND-CONQUER FACIAL NERVE SEGMENTATION METHOD AND DEVICE

This is a U.S. national stage application of PCT Application No. PCT/CN2022/076927 under 35 U.S.C. 371, filed Feb. 18, 2022 in Chinese, claiming priority of Chinese Application No. 202111106992.2, filed Sep. 22, 2021, all of which are hereby incorporated by reference.

FIELD OF TECHNOLOGY

The present invention relates to the field of medical image processing, and in particular to a decoupling divide-and-conquer facial nerve segmentation method and a device thereof.

BACKGROUND TECHNOLOGY

Robotic cochlear implantation, an automatic treatment method to help patients restore hearing, relies on precise preoperative planning to avoid damaging a critical anatomical structure. It is crucial to identify the peri-cochlear tissue structure in the preoperative path planning. The facial nerve is the most important tissue structure around the cochlea and is less than 1 mm away from the surrounding tissue. If the peri-cochlear tissue structure is identified incorrectly, the temporofacial nerve is likely to be paralyzed permanently. Moreover, the accurate segmentation of the facial nerve faces two major challenges: (1) The facial nerve structure is quite small. The facial nerve occupies only a quite small region in the CT image (the image proportion of the facial nerve region of 9-16 pixels to the whole brain CT image of 512×512 pixels is 0.0034%). (2) A contrast between the facial nerve and a surrounding tissue structure is low. The boundary between the facial nerve and the surrounding environment is usually blurred and lacks the strong contrast required by the traditional segmentation methods. In conclusion, automatic and accurate facial nerve segmentation is a major challenge in preoperative path planning of the robotic cochlear implantation.

Traditional methods of facial nerve segmentation rely on manually extracting features such as a centerline and a set point. In these methods, generally, a classifier is trained to distinguish the facial nerve from a complex structure, with a high mis-segmentation rate. This is caused by the following reason: The inter-class difference between the facial nerve region and the surrounding highly-similar region is small, resulting in limited representational power for artificial feature extraction, as shown in the document: Noble J H, Warren F M, Labadie R F, et al. Automatic segmentation of the facial nerve and chorda tympani using image registration and statistical priors[C]//Medical Imaging 2008: Image Processing. International Society for Optics and Photonics, 2008, 6914: 69140P.

In recent years, with the development of deep learning, major breakthroughs have been made in medical image analysis. Especially the Unet model, which uses multi-level information to reconstruct high-resolution feature maps, converges on the premise of a small amount of data, and promotes the development of medical image segmentation. However, the features in the decoder based on the U-shaped model are highly dependent on the features extracted from the encoder. In these methods, features are directly introduced from the encoder to the decoder, ignoring the effectiveness of aggregation of features at different levels, limiting the effective use of features, and introducing misleading features, thereby resulting in confusion of the facial nerve with another region. In the existing facial nerve segmentation methods based on deep learning, as shown in the document: Ronneberger O, Fischer P, Brox T. U-net: Convolutional networks for biomedical image segmentation [C]//International Conference on Medical image computing and computer-assisted intervention. Springer, Cham, 2015: 234-241, the Dice coefficient of the segmentation precision of the used the Unet model is 0.756. As shown in the document: Zhou Z, Siddiquee M M R, Tajbakhsh N, et al. Unet++: A nested u-net architecture for medical image segmentation[M]//Deep learning in medical image analysis and multimodal learning for clinical decision support. Springer, Cham, 2018: 3-11, the Dice coefficient of the segmentation accuracy of the used Unet++ model is 0.764.

SUMMARY OF INVENTION

In view of the above, an object of the present invention is to provide a decoupling divide-and-conquer facial nerve segmentation method and a device thereof. The method and device resolve the impact of the small facial-nerve structure and a low contrast on the segmentation, improve the precision and speed of automatic facial nerve segmentation, and meet the needs of preoperative path planning for robotic cochlear implantation.

Embodiments provide a decoupling divide-and-conquer facial nerve segmentation method, including the following steps:

obtaining and pre-processing a computed tomography (CT) image, to obtain a sample set;

constructing a facial nerve segmentation model including a feature extraction module, a rough segmentation module, and a fine segmentation module, where the feature extraction module is configured to extract a feature from an inputted CT image sample, to obtain one low-level feature map and a plurality of different- and high-level feature maps; the rough segmentation module includes a search identification module and a pyramid fusion module, the search identification module is configured to perform global facial nerve search on the plurality of different- and high-level feature maps that are juxtaposed, to obtain a plurality of facial nerve feature maps, and the pyramid fusion module is configured to fuse the plurality of facial nerve feature maps to obtain a fused feature map; the fine segmentation module includes a decoupling module and a spatial attention module, the decoupling module is configured to perform feature-space conversion on the fused feature map, to obtain a central body feature map, the central body feature map is combined with the low-level feature map to obtain an edge-detail feature map, the spatial attention module is configured to extract an attention feature from each of the central body feature map and the edge-detail feature map, to obtain extraction results, and the extraction results are fused and then are processed by the spatial attention module, to obtain a facial nerve segmentation image;

constructing a loss function, where the loss function includes a difference between the fused feature map and an original label of the CT image sample, a difference between the facial nerve segmentation image and the original label of the CT image sample, a difference between a prediction result of processing the central body feature map by the spatial attention module and a body label, and a difference between a prediction result of processing the edge-detail feature map by the spatial attention module and a detail label; and optimizing a parameter of the facial nerve segmentation model by using the sample set and the loss function, and then performing facial nerve segmentation on the inputted CT image by using the facial nerve segmentation model determined based on the parameter, to obtain a facial nerve segmentation image.

In an embodiment, the feature extraction module uses an improved Res2Net50, all fully connected layers and a last convolution set of an original Res2Net50 are removed, a plurality of remaining convolution sets form the improved Res2Net50, the inputted CT image sample is inputted into the Res2Net50, an output of a first convolution set is the low-level feature map, and outputs of other convolution sets are the different- and high-level feature maps respectively.

In an embodiment, a process of the global facial nerve search by the search identification module on the high-level feature maps includes:

dividing the high-level feature maps according to channels, to obtain divided feature maps; performing multi-branch operation on the divided feature maps, performing convolution operation on the divided feature maps in a first branch and remaining branches to convert a quantity of the channels, performing asymmetric convolution operation and dilated convolution operation on the divided feature maps in the remaining branches, and fusing operation results of the feature maps in all the branches, to dilate the high-level feature maps; and performing inverse operation on the fusion result for dividing, to reconstruct features, thereby obtaining the facial nerve feature maps.

In an embodiment, the decoupling module performs the feature-space conversion on the fused feature map by using a space conversion model, to obtain the central body feature map, and a process of the feature-space conversion includes parameter predicting, coordinate mapping, and pixel sampling, wherein a process of the parameter predicting includes: converting and predicting the fused feature map by using a convolutional layer, to obtain a parameter matrix;

a process of the coordinate mapping includes: using an element value in the parameter matrix as an offset of a pixel, and mapping coordinates of a pixel of the fused feature map in a standard space network by using the offset, to obtain a newly-fused feature map; and a process of the pixel sampling includes: sampling the newly-fused feature map by using a differentiable bilinear sampling mechanism, to obtain the central body feature map formed by pixels.

In an embodiment, the step of combining the central body feature map with the low-level feature map to obtain the edge-detail feature map includes:

performing, by the search identification module, global facial nerve search on the low-level feature map to obtain the facial nerve feature map, calculating a difference between the central body feature map and the fused feature map, splicing the difference with the facial nerve feature map, and fusing convolutional layers to obtain the edge-detail feature map.

In an embodiment, a process of extracting the attention feature from the inputted image by the spatial attention module is:

performing convolution operation and global average pooling operation on the inputted image, performing screening by using a threshold mechanism formed by an activation layer and a fully connected layer, and performing activating by using an activation function, to obtain a prediction result of extracting an attention feature corresponding to the inputted image, where the inputted image is a fused result of prediction results of extracting two attention features corresponding to the central body feature map and the edge-detail feature map, the central body feature map, and the central body feature map.

In an embodiment, a process of constructing the body label and the detail label of the CT image sample includes:

dividing the original label I of the CT image into a foreground $I_{fg}$ and a background $I_{bg}$, calculating a distance between a pixel p in the foreground $I_{fg}$ and a pixel q in the background $I_{bg}$, and obtaining a converted label I' by using the following distance conversion function:

$$I' = \begin{cases} \min_{q \in I_{bg}} f(p, q) & p \in I_{fg} \\ 0 & p \in I_{bg} \end{cases}$$

normalizing the converted label I', to obtain a normalized label I":

$$I'' = \frac{I' - \min(I')}{\max(I') - \min(I')}$$

determining, according to the normalized label I", the body label $I_b$ and the detail label $I_d$ of the CT image to be:

$$I_b = I * I'' \quad I_d = I * (I - I'') \text{ respectively.}$$

In an embodiment, the loss function is expressed as:

$$L = \sum_{i=1}^{2} L(p^i, I) + L_{bce}(p_b, I_b, \alpha) + L_{bce}(p_d, I_d, \alpha) L(p^i, I) =$$

$$L_{bce}(p^i, I, \alpha) + L_{iou}(p^i, I, \alpha)$$

wherein L(·) represents a cross-entropy loss function. $L_{iou}(\cdot)$ represents an intersection loss function, $p_b$ represents the prediction result of processing the central body feature map by the spatial attention module, $I_b$ represents the body label, $p_d$ represents the prediction result of processing the edge-detail feature map by the spatial attention module, $I_d$ represents the detail label, $\alpha$ represents a weight factor, I represents the original label of the CT image, and $p^1$ and $p^2$ represent the fused feature map and the facial nerve segmentation image, respectively.

In an embodiment, the step of pre-processing CT image includes: enhancing data through random flipping and cutting, and taking the data-enhanced CT image as the sample set.

The embodiments further provide a decoupling divide-and-conquer facial nerve segmentation device, including a memory, a processor, a computer program stored in the memory and executable by the processor. When executing the computer program, the processor performs the steps of the decoupling divide-and-conquer facial nerve segmentation method.

The decoupling divide-and-conquer facial nerve segmentation method and device provided by the embodiments have at least the following beneficial effects:

As for the characteristics of a small facial nerve structure and a low contrast, a facial nerve segmentation model including a feature extraction module, a rough segmentation module, and a fine segmentation module is constructed. The feature extraction module is configured to extract a low-level feature and a plurality of different- and high-level features. The rough segmentation module is configured to globally search the different- and high-level features for facial-nerve features and fuse them. The fine segmentation module is configured to decouple a fused feature to obtain a central body feature. After the central body feature is combined with the low-level feature to obtain an edge-detail feature, a space attention mechanism is used to extract attention features from the central body feature and the edge-detail feature, to obtain a facial nerve segmentation image. The method improves the precision and speed of automatic facial nerve segmentation, and meets the needs of preoperative path planning for robotic cochlear implantation.

BRIEF DESCRIPTION OF THE DRAWINGS

In order to illustrate the embodiments of the present invention or the technical solutions in the prior art more clearly, the following briefly introduces the accompanying drawings used in the description of the embodiments or the prior art. Obviously, the drawings in the following description are only some embodiments of the present invention. For those of ordinary skill in the art, other drawings can also be obtained from these drawings without creative efforts.

DETAILED DESCRIPTION OF THE EMBODIMENTS

In order to make the purpose, technical solutions and advantages of the present invention more understandable, the present invention is further described below in detail with reference to the accompanying drawings and embodiments. It should be understood that the specific implementations described herein are only used to explain the present invention rather than limiting the protection scope of the present invention.

As for the characteristics of a small facial-nerve structure and a low contrast, to resolve the problems of a highly incorrect rate and a low speed of the traditional facial nerve segmentation, embodiments provide a decoupling divide-and-conquer facial nerve segmentation method.

Figure 1:
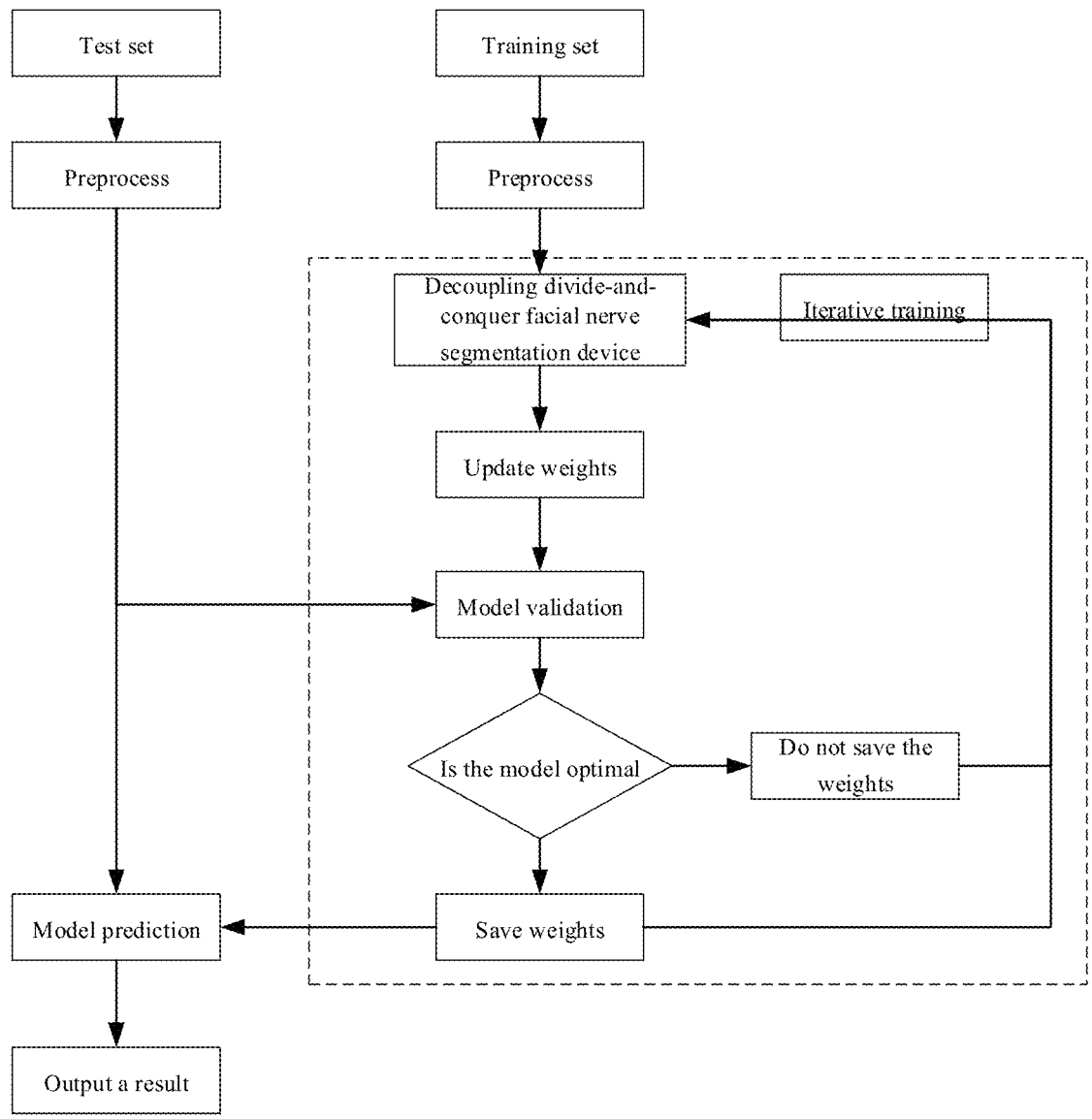
FIG. 1 is a flowchart of a decoupling divide-and-conquer facial nerve segmentation method according to an embodiment of the present invention.

FIG. 1 is a flowchart of a decoupling divide-and-conquer facial nerve segmentation method according to an embodiment of the present invention. As shown in FIG. 1, the decoupling divide-and-conquer facial nerve segmentation method provided in the embodiments mainly includes two phases: training and testing. First, all acquired CT image data is randomly divided into a training set and a test set. In the training phase, the training set is used for training. The training set is pro-processed by enhancing data through flipping, cutting, and the like. Next, the data-enhanced training samples are inputted into the facial nerve segmentation model, and the parameter of the facial nerve segmentation model is updated. Then, the trained facial nerve segmentation model is verified. The test set is pro-processed by enhancing data through flipping, cutting, and the like. The test samples with enhanced data are inputted into the facial nerve segmentation model, and the prediction result outputted by the facial nerve segmentation model is evaluated, to determine whether the facial nerve segmentation model is optimal. If it is, the model parameter is stored; and otherwise, the data is not stored. This is done iteratively. In the testing phase, the optimal parameter is loaded into the facial nerve segmentation model for testing, and then the prediction result is outputted.

Figure 2:
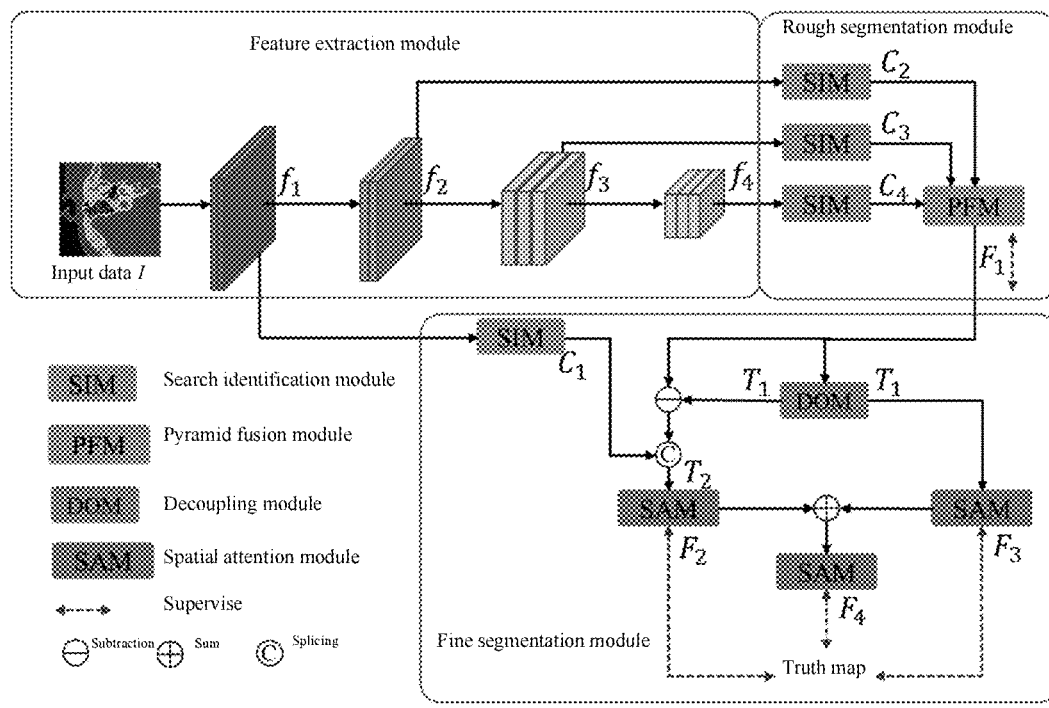
FIG. 2 is a structural diagram of a facial nerve segmentation model according to an embodiment of the present invention.

FIG. 2 is a structural diagram of a facial nerve segmentation model according to an embodiment of the present invention. As shown in FIG. 2, the facial nerve segmentation model provided in the embodiment includes a feature extraction module, a rough segmentation module, and a fine segmentation module.

The feature extraction module is configured to extract a feature from an inputted CT image sample, to obtain one low-level feature map and a plurality of different- and high-level feature maps. In an embodiment, an improved Res2Net50 is used as the backbone network of the feature extraction module. For the implementation of the facial nerve segmentation task, all fully connected layers and the last one convolution set of the original Res2Net50 are removed, and the remaining four convolution sets form the improved Res2Net50. The inputted CT image sample is expressed as $I \in R^{H \times W \times c}$, wherein H represents a height, W represents a width, c represents a quantity of channels, and c=1. The Res2Net50 extracts different-level feature maps based on the formula: $\{f_j\}_{j=1}^{4}$. Because the facial-nerve region is small, in the embodiment, the stride of the second convolutional layer of the backbone network is set to 1. To reserve larger resolution, the resolution of the feature map in each layer is set to $\{[H/k, W/k], k=2,2,4,8\}$. Recent studies have shown that a deeper layer of the network is more likely to extract the low-frequency object location information of the target, and a shallower layer is more likely to retain the high-frequency detailed information in the image. Therefore, in the embodiments, the extracted features are divided into high-level feature maps $f_2$, $f_3$, $f_4$ and a low-level feature map $f_1$.

The rough segmentation module includes a search identification module and a pyramid fusion module. The search identification module performs global facial nerve search on three high-level feature maps $f_2$, $f_3$, $f_4$ respectively, and obtains facial nerve feature maps $C_2$, $C_3$, $C_4$ by capturing a small item through an extended receptive field. In addition, the efficient pyramid fusion module fuses the facial nerve feature maps $C_2$, $C_3$, $C_4$ to obtain a fused feature map.

Figure 3:
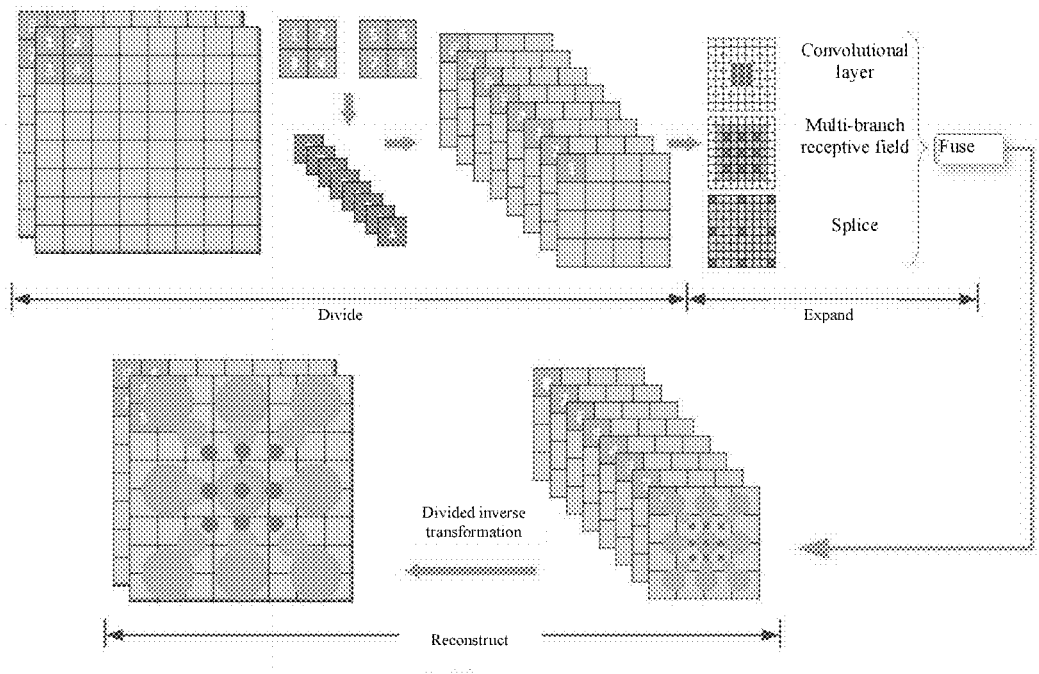
FIG. 3 is a schematic structural diagram of a search identification module according to an embodiment of the present invention.

FIG. 3 is a schematic structural diagram of a search identification module according to an embodiment of the present invention. As shown in FIG. 3, the search identification module searches a high-level feature map of N×N×c for a 2×2×c patch by using a sliding window of 2×2, and the patches, according to channels, are arranged, such that the high-level feature maps are divided according to the channels. Each patch is disassembled and converted to 4 channels. Therefore, after the dividing, a feature map of N/2×N/2×4c can be obtained. Each point in the feature map represents four feature points in the original high-level feature map. Then, the receptive field is used to process the feature map of each channel. The receptive fields include four branches for feature maps of four channels. A first branch performs convolution operation on the feature map of a first channel by using a convolutional layer of 1×1, to convert a quantity of the channels to 32. After the remaining branches perform convolution operation on feature maps of the remaining three channels by using a convolutional layer of 1×1, to convert the quantity of the channels to 32, asymmetric convolution operation and dilated convolution operation with a corresponding convolution kernel are performed, to splice and fuse the processing results of the four branches, thereby dilating the high-level feature maps. At last, an inverse operation is performed on the spliced and fused result for dividing, to reconstruct the feature, and obtain the facial nerve feature map. In this way, the receptive fields of the neural network are expanded by dividing, dilating, and reconstructing the high-level feature maps, to search for the facial nerve in a global range, and obtain an accurate facial nerve feature map.

Figure 4:
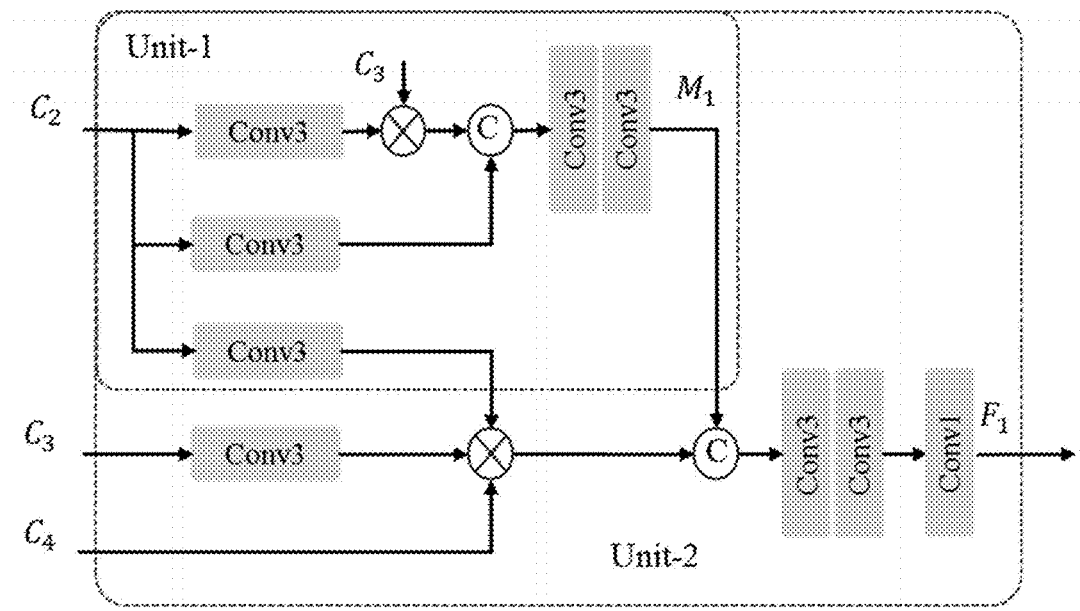
FIG. 4 is a schematic structural diagram of a pyramid fusion module according to an embodiment of the present invention.

To further enhance the expressive ability of high-level features, the pyramid fusion module fuses the facial nerve feature maps $C_2$, $C_3$, $C_4$ to obtain a fused feature map. As shown in FIG. 4, the pyramid fusion module includes a first unit Unit-1 and a second unit Unit-2. The first unit Unit-1 performs, by using three different convolutional layers, a convolution operation on a facial nerve feature map $C_2$ including high-level semantic information and low-level detailed information, to obtain three feature maps $\alpha, \beta, \gamma$, and then multiplies the feature map $C_3$ with the facial nerve feature map $C_3$ to test self-similarity. Subsequently, the Unit-1 connects the obtained feature to the feature map $\beta$ to obtain a feature map $M_1$, where the feature map $M_1$ retains more information, and finally smoothes the feature map $M_1$ by using two convolutional layers, to obtain a smooth $M_1$. The second unit Unit-2 performs convolution operation on the facial nerve feature map $C_3$, and then multiplies the obtained feature map with the facial nerve feature map $C_4$ to obtain $C_{34}$, and constructs a strong feature by using a product of $\gamma$ and $C_{34}$. Subsequently, the Unit-2 splices the strong feature and the smooth $M_1$, smoothes the spliced result by using two convolutional layers, and compresses the quantity of channels to 32 by using a convolutional layer, to output a fused feature map $F_1$.

The fine segmentation module includes a decoupling module and a spatial attention module. The decoupling module performs feature-space conversion on the fused feature map, to obtain a central body feature map $T_1$. The central body feature map is combined with the low-level feature map to obtain an edge-detail feature map $T_2$. The spatial attention module extracts an attention feature from the central body feature map $T_1$, to obtain a prediction result $F_3$. The spatial attention module extracts an attention feature from the edge-detail feature map $T_2$, to obtain a prediction result $F_2$. After processing the fused result between the prediction results $F_2$ and $F_3$, the spatial attention module outputs a facial nerve segmentation image $F_4$.

The decoupling module performs the feature-space conversion on the fused feature map by using a space conversion model, to obtain the central body feature map $T_1$. A process of the feature-space conversion includes parameter predicting, coordinate mapping, and pixel sampling. During the parameter predicting, a convolutional layer with a convolution kernel of 3×3 is used to convert and predict the inputted fused feature map $F_1 \in R^{H \times W \times c}$, to obtain a parameter matrix $\theta \in R^{H \times W \times c_1}$, wherein $c_1 = 2$ represents conversion matrixes that have a same size with two channels. During the coordinate mapping, an element value in the parameter matrix is used as an offset of a pixel. Coordinates of a pixel of the fused feature map in a standard space network are mapped by using the offset, to obtain a newly-fused feature map, that is, a pixel $p_l$ of the fused feature map in the standard space network is mapped to a new pixel $\hat{p}$ in a warped space grid through $p_l + \theta(p_l)$, thereby mapping coordinates. The new pixel $\hat{p}$ forms a newly fused feature map. During the pixel sampling, the newly-fused feature map is sampled by using a differentiable bilinear sampling mechanism, to obtain the central body feature map $T_1$ formed by pixels, that is, the differentiable bilinear sampling mechanism proposed in a spatial transformer network is used to approximate each pixel in the central body feature map by linearly interpolating values of four adjacent pixels closest to the pixel $p_l$.

To obtain the edge-detail feature map, a difference between the original fused feature map and the obtained central body feature map is used to extract a detail feature map. However, because of the characteristics of the backbone network, a low-level feature map $f_1$ in its shallow layer mainly includes low-level features in the image, and includes more detailed information. Therefore, a combination between the foregoing detail feature map and the low-level feature map $f_1$ is used as the edge-detail feature map $T_2$ of a facial nerve. The specific process is that the search identification module performs global facial nerve search on the low-level feature map $f_1$ to obtain the facial nerve feature map $C_1$, calculates a difference between the central body feature map and the fused feature map, splices the difference with the facial nerve feature map $C_1$, and fuses convolutional layers to obtain the edge-detail feature map $T_2$.

The spatial attention module mainly optimizes the central body feature map $T_1$ and the edge-detail feature map $T_2$, and obtains the final facial nerve segmentation image. Due to the output of the convolutional layer, the relative dependency of positions between the central body feature map and the edge-detail feature map is not considered. To make the facial nerve segmentation model selectively enhance a feature with large amount of information, and suppress a feature with small amount of information or a useless one, the spatial attention module processes the central body feature map $T_1$ and the edge-detail feature map $T_2$. The specific processing process is that the feature signal of each of positions in the central body feature map $T_1$ and the edge-detail feature map $T_2$ is examined. A location descriptor of which the global information is a feature is compressed through convolution operation. Then, the global average pooling operation is used to extract the statistics of each channel. To enhance the generalization ability of extracted features, a threshold mechanism formed by one activation layer and two fully connected layers is used to further screen the features. Next, an activation function is used to calculate the dependence degree of each position, to learn the non-mutually exclusive relationship between features. In addition, the effect of a plurality of channels on the facial nerve segmentation features is reduced, to obtain prediction results $F_3$ and $F_2$ of extracting attention features corresponding to the central body feature map $T_1$ and the edge-detail feature map $T_2$. Subsequently, the feature map f is obtained by summing the prediction results $F_3$ and $F_2$. Finally, the spatial attention module processes the feature map $\hat{F}$, to obtain the facial nerve segmentation image $F_4$.

Figure 5:
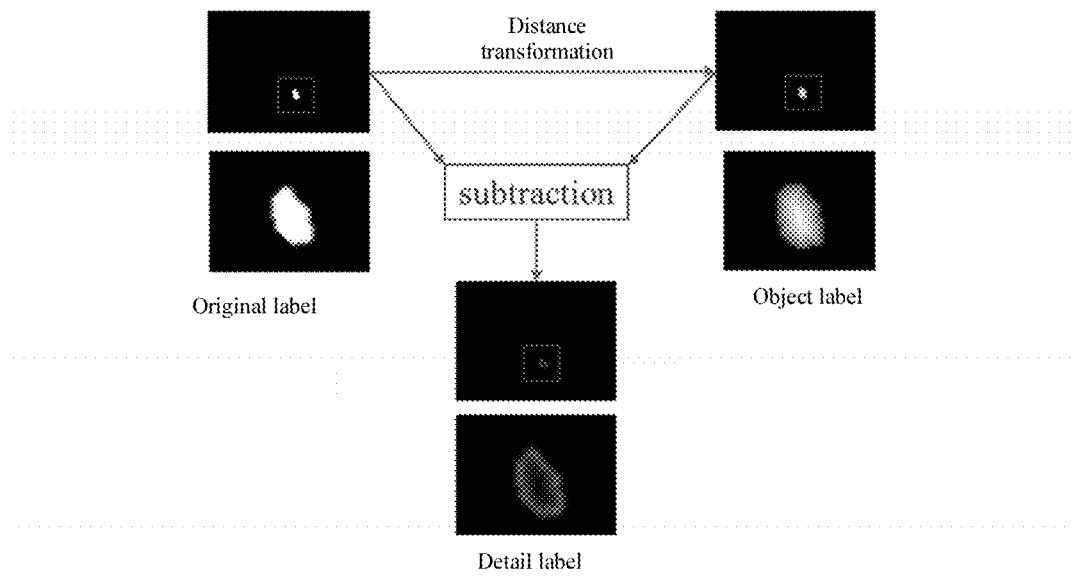
FIG. 5 is a schematic diagram of a body label and a detail label according to an embodiment of the present invention.

The prediction difficulty of a pixel is closely related to its location. Due to the cluttered grayscale value of the CT image, adjacent pixels around the edge of a facial nerve are more likely to be mispredicted. In contrast, a center pixel has a higher prediction accuracy due to the consistency in the facial nerve. These pixels are processed according to their individual characteristics. Therefore, as shown in FIG. 5, in the embodiments, the original label is decoupled into a body label and a detail label. A distance conversion function may convert a binary image into a new image. Each foreground pixel has a minimum distance from the background.

Specifically, the original label I of the CT image is divided into a foreground $I_{fg}$ and a background $I_{bg}$, a distance between a pixel p in the foreground $I_{fg}$ and a pixel q in the background $I_{bg}$ is calculated, and a converted label I' is obtained by using the following distance conversion function:

$$I' = \begin{cases} \min_{q \in I_{bg}} f(p, q) & p \in I_{fg} \\ 0 & p \in I_{bg} \end{cases}$$

The converted label I' is normalized, to obtain a normalized label I":

$$I'' = \frac{I' - \min(I')}{\max(I') - \min(I')}$$

The converted label I' is in a form of a matrix. During the normalizing, I'−min(I') represents that min(I') is subtracted from each element value in the matrix I', and then the obtained result is compared with the difference between max(I') 和 min(I') to obtain the normalized result I".

The pixel in the normalized label I" is not distinguished based on the foreground or background, and a pixel value closer to the center of the foreground is higher. Therefore, after multiplied with the original label, the normalized label I" is used as the body label $I_b$ of the foreground. The detail label $l_d$ of an edge detail part may be obtained through calculation on the original label by using the following formula:

$$I_b = I * I'' \quad I_d = I * (I - I'')$$

The original label is decoupled into two different labels, which are used to supervise and help the network to learn the central body features and edge detail features of different features respectively.

Figure 6:
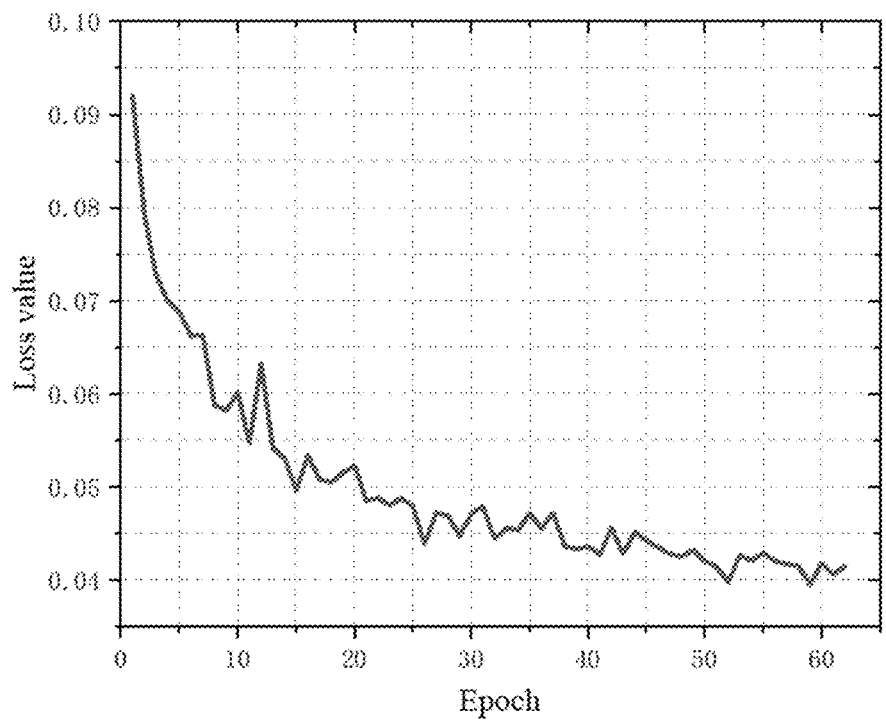
FIG. 6 is a graph of a loss function according to an embodiment of the present invention.

To optimize the network parameters of the facial nerve segmentation model, a loss function needs to be constructed. The constructed loss function includes four parts, namely, a difference between the fused feature map and an original label of the CT image sample, a difference between the facial nerve segmentation image and the original label of the CT image sample, a difference between a prediction result of processing the central body feature map by the spatial attention module and a body label, and a difference between a prediction result of processing the edge-detail feature map by the spatial attention module and a detail label. The loss function is specifically expressed as:

$$L = \sum_{i=1}^{2} L(p^i, I) + L_{bce}(p_b, I_b, \alpha) + L_{bce}(p_d, I_d, \alpha) L(p^i, I) = \\ L_{bce}(p^i, I, \alpha) + L_{iou}(p^i, I, \alpha)$$

wherein $L_{iou}(\cdot)$ represents a cross-entropy loss function, $L_{bce}(\cdot)$ represents an intersection loss function, $p_b$ represents the prediction result of processing the central body feature map by the spatial attention module, $I_b$ represents the body label, $p_d$ represents the prediction result of processing the edge-detail feature map by the spatial attention module, $E_d$ represents the detail label, α represents a weight factor, I represents the original label of the CT image, and $p^1$ and $p^2$ represent the fused feature map and the facial nerve segmentation image respectively. The loss function curve during the training is shown in FIG. 6.

When the loss function is used to train the facial nerve segmentation model, the Adam optimizer is used to optimize the model, and the initial learning rate is set to 1e-4, which is reduced 10 times every 60 rounds. The inputted image is resized to 352×352, and the multi-scale is used for training with the scaling rate (0.5, 0.75, 1, 1.25, and 1.5). All training samples are enhanced through random flipping, rotating, and boundary clipping.

Figure 7:
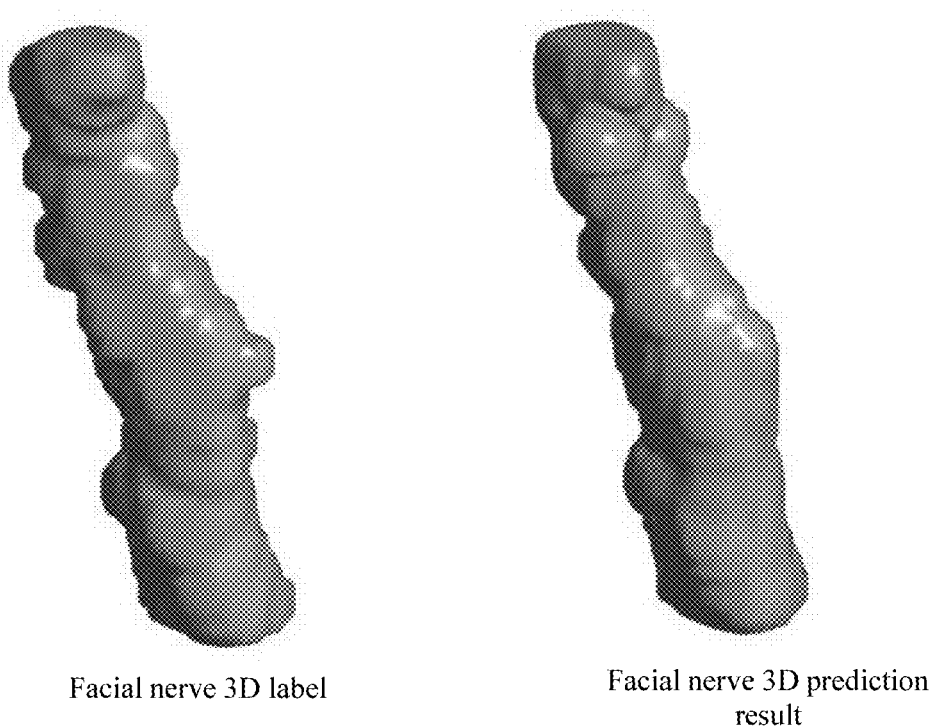
FIG. 7 is a schematic diagram of a segmentation result according to an embodiment of the present invention.
Figure 8:
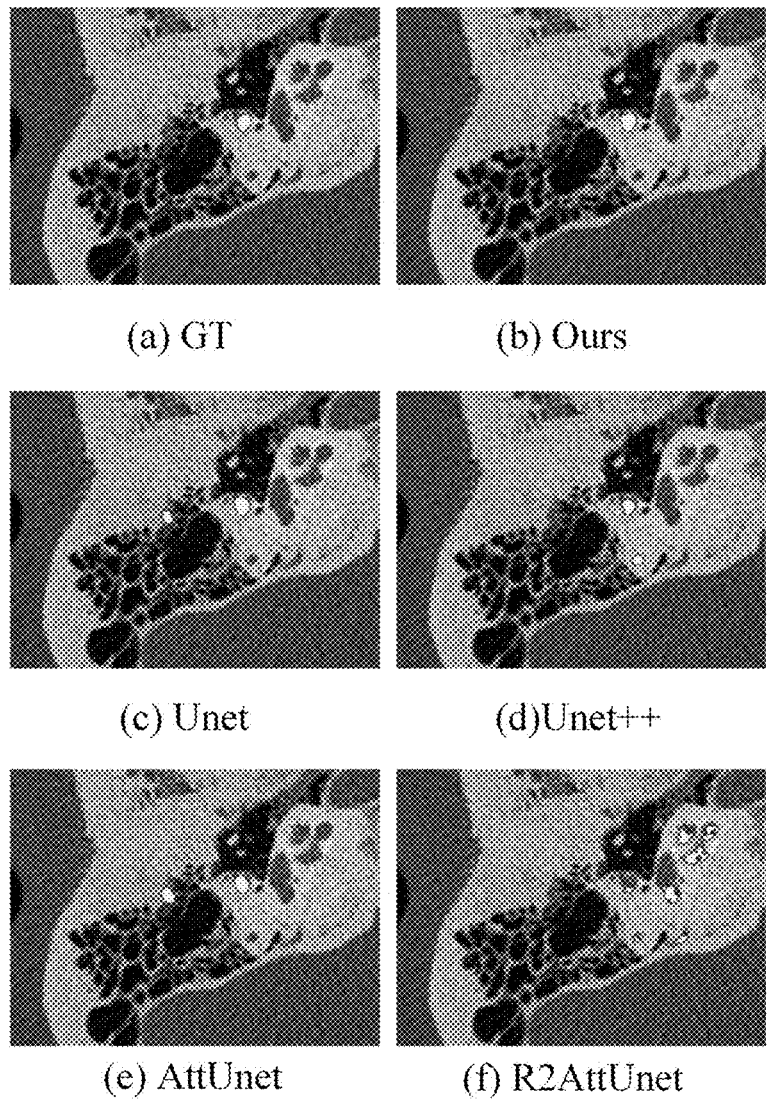
FIG. 8 is a comparison diagram between segmentation results of methods according to an embodiment of the present invention.
Figure 9:
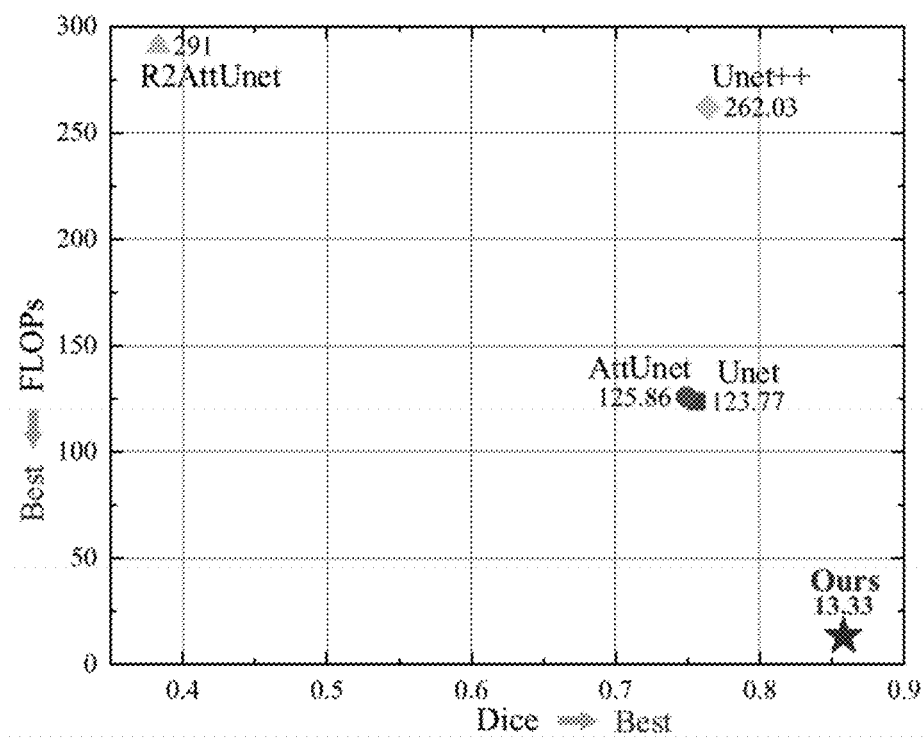
FIG. 9 is a schematic diagram of an outcome indicator Dice score and floating-point operations per second (FLOPs) according to an embodiment of the present invention.

This embodiment also presents the implementation result of the decoupling divide-and-conquer facial nerve segmentation method. As shown in FIG. 7, the facial nerve segmentation result obtained by the facial nerve segmentation model provided in the embodiments and the manual segmentation result are basically consistent, indicating the accuracy of the facial nerve segmentation model of the method. As shown in FIG. 1, compared with the results of the classic Unet model, Unet++ model, AttUnet model, and R2AttUnet model, the facial nerve segmentation model Ours has a stable improvement in all indicators, the Dice coefficient is 0.858, and 95% of the Hough distance is 0.363. In terms of computational complexity, the computational power requirement (FLOPs) of the facial nerve segmentation model is only 13.33 G, less than 1/10 of that of theUnet (123.77 G), and the quantity of parameters (9.86 M) is only about ¼ of that of the Unet (34.53 M). As shown in FIG. 8, it can be seen that from the 2D result of segmenting the facial nerves by each model, compared with other methods, the facial nerve segmentation model Ours is more accurate, and does not identify another tissue as a facial nerve, avoiding incorrect segmentation. In addition, the edge of the segmentation result of the facial nerve segmentation model Ours is closer to the label. As shown in FIG. 9, the computational complexity and the Dice score of the facial nerve segmentation model are both optimal.

TABLE 1

| Model | Dice | Jacc | AHD | HD | HD95 | ASSD | SSD | Prec | recall |
|---|---|---|---|---|---|---|---|---|---|
| Unet | 0.756 | 0.629 | 0.443 | 3.553 | 3.223 | 0.665 | 1.145 | 0.684 | 0.907 |
| AttUnet | 0.749 | 0.624 | 0.568 | 3.701 | 3.401 | 0.736 | 1.300 | 0.677 | 0.898 |
| R2AttUnet | 0.383 | 0.259 | 3.284 | 18.349 | 16.027 | 3.742 | 7.041 | 0.310 | 0.601 |
| Unet++ | 0.764 | 0.643 | 0.701 | 4.263 | 3.737 | 0.878 | 1.548 | 0.779 | 0.814 |
| Ours | 0.858 | 0.764 | 0.039 | 0.491 | 0.363 | 0.128 | 0.134 | 0.874 | 0.868 |

The embodiments further provide a decoupling divide-and-conquer facial nerve segmentation device, including a memory, a processor, a computer program stored in the memory and executable by the processor. When executing the computer program, the processor performs the steps of the decoupling divide-and-conquer facial nerve segmentation method.

In practical application, the computer memory may be a near-end volatile memory such as a random-access memory, a non-volatile memory such as a read-only memory, a FLASH, a floppy disk, and mechanical hard disk, or a remote storage cloud. The computer processor may be a central processing unit, a microprocessor, a digital signal processor, or a field-programmable gate array, that is, these processors can perform the steps of the decoupling divide-and-conquer facial nerve segmentation method.

In the foregoing specific implementations, the technical solutions and beneficial effects of the present invention are described in detail. It should be understood that the above descriptions are only the most preferable embodiments of the present invention, and are not intended to limit the present invention. Any modifications, additions and equivalent replacements made within the scope of the principles of the present invention shall fall into the protection scope of the present invention.

The invention claimed is:

1. A decoupling divide-and-conquer facial nerve segmentation method, comprising the following steps:

obtaining and pre-processing a computed tomography (CT) image to obtain a sample set;

constructing a facial nerve segmentation model comprising a feature extraction module, a rough segmentation module, and a fine segmentation module, wherein the feature extraction module is configured to extract a feature from an inputted CT image sample, to obtain one low-level feature map and a plurality of different- and high-level feature maps; the rough segmentation module comprises a search identification module and a pyramid fusion module, the search identification module is configured to perform global facial nerve search on the plurality of different- and high-level feature maps that are juxtaposed, to obtain a plurality of facial nerve feature maps, and the pyramid fusion module is configured to fuse the plurality of facial nerve feature maps to obtain a fused feature map; the fine segmentation module comprises a decoupling module and a spatial attention module, the decoupling module is configured to perform feature-space conversion on the fused feature map, to obtain a central body feature map, the central body feature map is combined with the low-level feature map to obtain an edge-detail feature map, the spatial attention module is configured to extract an attention feature from each of the central body feature map and the edge-detail feature map, to obtain extraction results, and the extraction results are fused and then are processed by the spatial attention module, to obtain a facial nerve segmentation image;

constructing a loss function, wherein the loss function comprises a difference between the fused feature map and an original label of the CT image sample, a difference between the facial nerve segmentation image and the original label of the CT image sample, a difference between a prediction result of processing the central body feature map by the spatial attention module and a body label, and a difference between a prediction result of processing the edge-detail feature map by the spatial attention module and a detail label; and optimizing a parameter of the facial nerve segmentation model by using the sample set and the loss function, and then performing facial nerve segmentation on the inputted CT image by using the facial nerve segmentation model determined based on the parameter, to obtain a facial nerve segmentation image.

2. The decoupling divide-and-conquer facial nerve segmentation method according to claim 1, wherein the feature extraction module uses an improved Res2Net50, all fully connected layers and a last convolution set of an original Res2Net50 are removed, a plurality of remaining convolution sets form the improved Res2Net50, the inputted CT image sample is inputted into the Res2Net50, an output of a first convolution set is the low-level feature map, and outputs of other convolution sets are the different levels of high-level feature maps, respectively.

3. The decoupling divide-and-conquer facial nerve segmentation method according to claim 1, wherein a process of the global facial nerve search by the search identification module on the high-level feature maps comprises:

dividing the high-level feature maps according to channels, to obtain divided feature maps; performing multi-branch operation on the divided feature maps, performing convolution operation on the divided feature maps in a first branch and remaining branches to convert a quantity of the channels, performing asymmetric convolution operation and dilated convolution operation on the divided feature maps in the remaining branches, and fusing operation results of the feature maps in all the branches, to dilate the high-level feature maps; and performing inverse operation on the fusion result for dividing, to reconstruct features, thereby obtaining the facial nerve feature maps.

4. The decoupling divide-and-conquer facial nerve segmentation method according to claim 1, wherein the decoupling module performs the feature-space conversion on the fused feature map by using a space conversion model, to obtain the central body feature map, and a process of the feature-space conversion comprises parameter predicting, coordinate mapping, and pixel sampling, wherein a process of the parameter predicting comprises: converting and predicting the fused feature map by using a convolutional layer, to obtain a parameter matrix;

a process of the coordinate mapping comprises: using an element value in the parameter matrix as an offset of a pixel, and mapping coordinates of a pixel of the fused feature map in a standard space network by using the offset, to obtain a newly-fused feature map; and a process of the pixel sampling comprises: sampling the newly-fused feature map by using a differentiable bilinear sampling mechanism, to obtain the central body feature map formed by pixels.

5. The decoupling divide-and-conquer facial nerve segmentation method according to claim 1, wherein the step of combining the central body feature map with the low-level feature map to obtain the edge-detail feature map comprises:

performing, by the search identification module, global facial nerve search on the low-level feature map to obtain the facial nerve feature map, calculating a difference between the central body feature map and the fused feature map, splicing the difference with the facial nerve feature map, and fusing convolutional layers to obtain the edge-detail feature map.

6. The decoupling divide-and-conquer facial nerve segmentation method according to claim 1, wherein a process of extracting the attention feature from the inputted image by the spatial attention module comprises:

performing convolution operation and global average pooling operation on the inputted image, performing screening by using a threshold mechanism formed by an activation layer and a fully connected layer, and performing activating by using an activation function, to obtain a prediction result of extracting an attention feature corresponding to the inputted image, wherein the inputted image is a fused result of prediction results of extracting two attention features corresponding to the central body feature map and the edge-detail feature map, the central body feature map, and the central body feature map.

7. The decoupling divide-and-conquer facial nerve segmentation method according to claim 1, wherein a process of constructing the body label and the detail label of the CT image sample comprises:

dividing the original label I of the CT image into a foreground $I_{fg}$ and a background $I_{bg}$, calculating a distance between a pixel p in the foreground $I_{fg}$ and a pixel q in the background $I_{bg}$, and obtaining a converted label I' by using the following distance conversion function:

$$I' = \begin{cases} \min_{q \in I_{bg}} f(p, q) & p \in I_{fg} \\ 0 & p \in I_{bg} \end{cases}$$

normalizing the converted label I', to obtain a normalized label I":

$$I'' = \frac{I' - \min(I')}{\max(I') - \min(I')}$$

determining, according to the normalized label I", the body label $I_b$ and the detail label $l_d$ of the CT image to be:

$$I_b = I * I'' \quad I_d = I * (I - I'') \text{ respectively.}$$

8. The decoupling divide-and-conquer facial nerve segmentation method according to claim 1, wherein the loss function is expressed as:

$$L = \sum_{i=1}^{2} L(p^i, I) + L_{bce}(p_b, I_b, \alpha) + L_{bce}(p_d, I_d, \alpha) L(p^i, I) =$$

$$L_{bce}(p^i, I, \alpha) + L_{iou}(p^i, I, \alpha)$$

wherein $L_{iou}$ represents a cross-entropy loss function, $L_{bce}(\cdot)$ represents an intersection loss function, $p_b$ represents the prediction result of processing the central body feature map by the spatial attention module, $I_b$ represents the body label, $p_d$ represents the prediction result of processing the edge-detail feature map by the spatial attention module, $l_d$ represents the detail label, $\alpha$ represents a weight factor, I represents the original label of the CT image, and $p^1$ and $p^2$ represent the fused feature map and the facial nerve segmentation image, respectively.

9. The decoupling divide-and-conquer facial nerve segmentation method according to claim 1, wherein the step of pre-processing CT image comprises: enhancing data through random flipping and cutting, and taking the data-enhanced CT image as the sample set.

10. A decoupling divide-and-conquer facial nerve segmentation device, comprising a memory, a processor, and a computer program stored in the memory and executable by the processor, wherein when executing the computer program, the processor performs the step of the decoupling divide-and-conquer facial nerve segmentation method according to claim 1.

* * * * *